US010350115B2

(12) United States Patent
Long et al.

(10) Patent No.: US 10,350,115 B2
(45) Date of Patent: Jul. 16, 2019

(54) ABSORBENT ARTICLE LEAKAGE ASSESSMENT SYSTEM

(71) Applicant: KIMBERLY-CLARK WORLDWIDE, INC., Neenah, WI (US)

(72) Inventors: Andrew M. Long, Neenah, WI (US); Shawn J. Sullivan, Neenah, WI (US); John C. Robertson, Neenah, WI (US); Richard N. Dodge, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/549,262

(22) PCT Filed: Feb. 26, 2016

(86) PCT No.: PCT/US2016/019672
§ 371 (c)(1),
(2) Date: Aug. 7, 2017

(87) PCT Pub. No.: WO2016/138331
PCT Pub. Date: Sep. 1, 2016

(65) Prior Publication Data
US 2018/0036180 A1    Feb. 8, 2018

Related U.S. Application Data

(60) Provisional application No. 62/126,001, filed on Feb. 27, 2015.

(51) Int. Cl.
*A61F 13/42* (2006.01)
*A61F 13/84* (2006.01)
(Continued)

(52) U.S. Cl.
CPC ........ *A61F 13/42* (2013.01); *A61F 13/49004* (2013.01); *G06K 9/00771* (2013.01);
(Continued)

(58) Field of Classification Search
CPC ................ A61F 13/42; A61F 2013/424; A61F 2013/8488; A61F 2013/8491
See application file for complete search history.

(56) References Cited

U.S. PATENT DOCUMENTS 3,460,123 A    8/1969    Bass
3,508,235 A    4/1970    Baisden
(Continued)

FOREIGN PATENT DOCUMENTS

CN    101196530 A    6/2008
DE    9309199 U1    8/1993
(Continued)

OTHER PUBLICATIONS

Yoon, Sung-Hoon and Xin-Sheng Chai, "Retention Rate Phenomena for Polyamide-Epichorohydrin Polymer in Papermaking Fibrous Colloidal Suspension," Journal of Industrial and Engineering Chemistry, vol. 13, No. 2, 2007, pp. 237-243.

*Primary Examiner* — Herbert K Roberts
(74) *Attorney, Agent, or Firm* — Kimberly-Clark Worldwide, Inc.

(57) ABSTRACT

A leakage assessment system for use with an absorbent article having an outer surface, the system including a computer and a signaling device adapted to be used in conjunction with the absorbent article, the signaling device adapted to sense wetness in the absorbent article, wherein the signaling device is in electronic communication with the computer. The system also includes a wetness detection mat in electronic communication with the computer, and an image capture device configured to continuously detect an absorbent article wearer position, wherein the image capture device is in electronic communication with the computer, wherein the computer is configured to electronically record wetness incidents using the signaling device, the wetness
(Continued)

detection mat, and the wearer position captured by the image capture device.

20 Claims, 2 Drawing Sheets

(51) Int. Cl.
  *G06K 9/00* (2006.01)
  *A61F 13/49* (2006.01)
  *G06K 9/62* (2006.01)

(52) U.S. Cl.
  CPC ...... *G06K 9/6214* (2013.01); *A61F 2013/424* (2013.01); *A61F 2013/8488* (2013.01); *A61F 2013/8491* (2013.01)

(56) References Cited

U.S. PATENT DOCUMENTS

| | | |
|---|---|---|
| 3,678,928 A | 7/1972 | Mozes |
| 3,778,570 A | 12/1973 | Shuman |
| 3,952,746 A | 4/1976 | Summers |
| 4,022,211 A | 5/1977 | Timmons et al. |
| 4,032,661 A | 6/1977 | Rowsell et al. |
| 4,068,221 A | 1/1978 | McClintock |
| 4,100,324 A | 7/1978 | Anderson et al. |
| 4,106,001 A | 8/1978 | Mahoney |
| 4,121,011 A | 10/1978 | Glover et al. |
| 4,136,163 A | 1/1979 | Watson et al. |
| 4,163,449 A | 8/1979 | Regal |
| 4,191,950 A | 3/1980 | Levin et al. |
| 4,192,311 A | 3/1980 | Felfoldi |
| 4,212,295 A | 7/1980 | Snyder |
| 4,230,688 A | 10/1980 | Rowsell et al. |
| 4,231,370 A | 11/1980 | Mroz et al. |
| 4,246,574 A | 1/1981 | Sanner |
| 4,252,845 A | 2/1981 | Griffiths et al. |
| 4,271,406 A | 6/1981 | Wilson |
| 4,347,503 A | 8/1982 | Uyehara |
| 4,356,479 A | 10/1982 | Wilson |
| 4,356,818 A | 11/1982 | Macias et al. |
| 4,459,425 A | 7/1984 | Amano et al. |
| 4,507,121 A | 3/1985 | Leung |
| 4,530,030 A | 7/1985 | Woest et al. |
| 4,539,559 A | 9/1985 | Kelly et al. |
| 4,571,750 A | 2/1986 | Barry |
| 4,610,678 A | 9/1986 | Weisman et al. |
| 4,642,250 A | 2/1987 | Spector |
| 4,653,491 A | 3/1987 | Okada et al. |
| 4,681,576 A | 7/1987 | Colon et al. |
| 4,704,108 A | 11/1987 | Okada et al. |
| 4,704,116 A | 11/1987 | Enloe |
| 4,705,513 A | 11/1987 | Sheldon et al. |
| 4,725,462 A | 2/1988 | Kimura |
| 4,738,260 A | 4/1988 | Brown |
| 4,744,113 A | 5/1988 | Kogut |
| 4,754,264 A | 6/1988 | Okada et al. |
| 4,768,023 A | 8/1988 | Xie |
| 4,796,014 A | 1/1989 | Chia |
| 4,800,370 A | 1/1989 | Vetecnik |
| 4,826,550 A | 5/1989 | Shimizu et al. |
| 4,834,733 A | 5/1989 | Huntoon et al. |
| 4,926,871 A | 5/1990 | Ganguly et al. |
| 4,940,464 A | 7/1990 | Van Gompel et al. |
| 4,977,906 A | 12/1990 | Di Scipio |
| 5,003,178 A | 3/1991 | Livesay |
| 5,036,859 A | 8/1991 | Brown |
| 5,043,704 A | 8/1991 | Blakeney |
| 5,060,638 A | 10/1991 | Bodine, Jr. |
| 5,066,711 A | 11/1991 | Colon et al. |
| 5,114,781 A | 5/1992 | Morman |
| 5,116,662 A | 5/1992 | Morman |
| 5,121,630 A | 6/1992 | Calvin |
| 5,137,033 A | 8/1992 | Norton |
| 5,144,284 A | 9/1992 | Hammett |
| 5,150,002 A | 9/1992 | Van Der Hoeck et al. |
| 5,151,092 A | 9/1992 | Buell et al. |
| 5,173,521 A | 12/1992 | Ishino |
| 5,174,656 A | 12/1992 | Dotan |
| 5,175,505 A | 12/1992 | Magenau et al. |
| 5,192,606 A | 3/1993 | Proxmire et al. |
| 5,197,958 A | 3/1993 | Howell |
| 5,221,228 A | 6/1993 | Pedroia |
| 5,224,769 A | 7/1993 | Holbrook et al. |
| 5,264,830 A | 11/1993 | Kline et al. |
| 5,266,592 A | 11/1993 | Grub et al. |
| 5,266,928 A | 11/1993 | Johnson |
| 5,284,703 A | 2/1994 | Everhart et al. |
| 5,291,181 A | 3/1994 | Deponte |
| 5,322,067 A | 6/1994 | Prater et al. |
| 5,341,127 A | 8/1994 | Smith |
| 5,341,673 A | 8/1994 | Burns et al. |
| 5,350,624 A | 9/1994 | Georger et al. |
| 5,354,289 A | 10/1994 | Mitchell et al. |
| H1376 H | 11/1994 | Osborn, III et al. |
| 5,384,411 A | 1/1995 | Robotti et al. |
| 5,389,093 A | 2/1995 | Howell |
| 5,392,032 A | 2/1995 | Kline et al. |
| 5,395,358 A | 3/1995 | Lu |
| 5,399,219 A | 3/1995 | Roessler et al. |
| 5,407,492 A | 4/1995 | Ohmi et al. |
| 5,416,469 A | 5/1995 | Colling |
| 5,454,376 A | 10/1995 | Stephens |
| 5,459,452 A | 10/1995 | Deponte |
| 5,469,145 A | 11/1995 | Johnson |
| 5,469,146 A | 11/1995 | Gurler |
| 5,475,835 A | 12/1995 | Hickey |
| 5,478,382 A | 12/1995 | Miller et al. |
| 5,486,166 A | 1/1996 | Bishop et al. |
| 5,486,227 A | 1/1996 | Kumar et al. |
| 5,490,846 A | 2/1996 | Ellis et al. |
| 5,537,095 A | 7/1996 | Dick et al. |
| 5,540,796 A | 7/1996 | Fries |
| 5,557,263 A | 9/1996 | Fisher et al. |
| 5,568,128 A | 10/1996 | Nair |
| 5,570,082 A | 10/1996 | Mahgerefteh et al. |
| 5,595,618 A | 1/1997 | Fries et al. |
| 5,617,488 A | 4/1997 | Hong et al. |
| 5,645,542 A | 7/1997 | Anjur et al. |
| 5,663,611 A | 9/1997 | Seats et al. |
| 5,702,377 A | 12/1997 | Collier, IV et al. |
| 5,709,222 A | 1/1998 | Davallou |
| 5,713,881 A | 2/1998 | Rezai et al. |
| 5,722,968 A | 3/1998 | Datta et al. |
| 5,760,694 A | 6/1998 | Nissim et al. |
| 5,766,389 A | 6/1998 | Brandon et al. |
| 5,768,696 A | 6/1998 | Law |
| 5,780,896 A | 7/1998 | Ono |
| 5,790,035 A | 8/1998 | Ho |
| 5,790,036 A | 8/1998 | Fisher et al. |
| 5,796,345 A | 8/1998 | Leventis et al. |
| 5,802,611 A | 9/1998 | McKenzie et al. |
| 5,808,554 A | 9/1998 | Shuminov |
| 5,817,076 A | 10/1998 | Fard |
| 5,820,973 A | 10/1998 | Dodge, II et al. |
| 5,838,240 A | 11/1998 | Johnson |
| 5,844,862 A | 12/1998 | Cocatre-Zilgien |
| 5,845,644 A | 12/1998 | Hughes et al. |
| 5,868,723 A | 2/1999 | Al-Sabah |
| 5,881,731 A | 3/1999 | Remes |
| 5,883,028 A | 3/1999 | Morman et al. |
| 5,902,296 A | 5/1999 | Fluyeras |
| 5,903,222 A | 5/1999 | Kawarizadeh et al. |
| 5,904,671 A | 5/1999 | Navot et al. |
| 5,922,537 A | 7/1999 | Ewart et al. |
| 5,931,823 A | 8/1999 | Stokes et al. |
| 5,959,535 A | 9/1999 | Remsburg |
| 5,962,995 A | 10/1999 | Avnery |
| 5,964,743 A | 10/1999 | Abuto et al. |
| 6,060,638 A | 5/2000 | Paul et al. |
| 6,066,774 A | 5/2000 | Roe |
| 6,093,869 A | 7/2000 | Roe et al. |
| 6,097,297 A | 8/2000 | Fard |
| 6,101,366 A | 8/2000 | Castillo |

(56) References Cited

U.S. PATENT DOCUMENTS

| | | |
|---|---|---|
| 6,110,111 A | 8/2000 | Barnard |
| 6,135,945 A | 10/2000 | Sultan |
| 6,149,636 A | 11/2000 | Roe et al. |
| 6,150,002 A | 11/2000 | Varona |
| 6,160,198 A | 12/2000 | Roe et al. |
| 6,163,262 A | 12/2000 | Wu |
| 6,186,991 B1 | 2/2001 | Roe et al. |
| 6,200,250 B1 | 3/2001 | Janszen |
| 6,231,557 B1 | 5/2001 | Krautkramer et al. |
| 6,246,330 B1 | 6/2001 | Nielsen |
| 6,270,783 B1 | 8/2001 | Slavtcheff et al. |
| 6,276,202 B1 | 8/2001 | Latarius |
| 6,297,424 B1 | 10/2001 | Olson et al. |
| 6,325,066 B1 | 12/2001 | Hughes et al. |
| 6,348,640 B1 | 2/2002 | Navot et al. |
| 6,359,190 B1 | 3/2002 | Ter-Ovanesyan et al. |
| 6,362,389 B1 | 3/2002 | McDowall et al. |
| 6,372,951 B1 | 4/2002 | Ter-Ovanesyan et al. |
| 6,373,263 B1 | 4/2002 | Netzer |
| 6,373,395 B1 | 4/2002 | Kimsey |
| 6,384,296 B1 | 5/2002 | Roe et al. |
| 6,384,728 B1 | 5/2002 | Kanor et al. |
| 6,392,542 B1 | 5/2002 | Stanley |
| 6,407,492 B1 | 6/2002 | Avnery et al. |
| 6,484,053 B2 | 11/2002 | Leelamanit et al. |
| 6,486,227 B2 | 11/2002 | Nohr et al. |
| 6,544,200 B1 | 4/2003 | Smith et al. |
| 6,552,245 B1 | 4/2003 | Roessler et al. |
| 6,559,772 B2 | 5/2003 | Zand et al. |
| 6,562,297 B1 | 5/2003 | Bonstein et al. |
| 6,580,013 B1 | 6/2003 | Belloso |
| 6,583,722 B2 | 6/2003 | Jeutter et al. |
| 6,603,403 B2 | 8/2003 | Jeutter et al. |
| 6,617,488 B1 | 9/2003 | Springer et al. |
| 6,627,233 B1 | 9/2003 | Wolf et al. |
| 6,635,797 B2 | 10/2003 | Olson et al. |
| 6,642,427 B2 | 11/2003 | Roe et al. |
| 6,645,190 B1 | 11/2003 | Olson et al. |
| 6,653,522 B1 | 11/2003 | Blumenthal et al. |
| 6,663,611 B2 | 12/2003 | Blaney et al. |
| 6,673,982 B1 | 1/2004 | Chen et al. |
| 6,677,859 B1 | 1/2004 | Bensen |
| 6,696,618 B2 | 2/2004 | Dodge, II et al. |
| 6,710,221 B1 | 3/2004 | Pierce et al. |
| 6,731,215 B2 | 5/2004 | Harms et al. |
| 6,733,766 B2 | 5/2004 | Gott et al. |
| 6,755,795 B2 | 6/2004 | Marmaropoulos et al. |
| 6,756,521 B1 | 6/2004 | Breitkopf |
| 6,772,454 B1 | 8/2004 | Barry et al. |
| 6,772,708 B2 | 8/2004 | Klofta et al. |
| 6,774,800 B2 | 8/2004 | Friedman et al. |
| 6,780,896 B2 | 8/2004 | MacDonald et al. |
| 6,870,479 B2 | 3/2005 | Gabriel |
| 6,904,865 B2 | 6/2005 | Klofta et al. |
| 6,929,819 B2 | 8/2005 | Underhill et al. |
| 6,970,091 B2 | 11/2005 | Roe |
| 7,002,054 B2 | 2/2006 | Allen et al. |
| 7,049,969 B2 | 5/2006 | Tamai |
| 7,141,715 B2 | 11/2006 | Shapira |
| 7,159,532 B2 | 1/2007 | Klofta et al. |
| 7,250,547 B1 | 7/2007 | Hofmeister et al. |
| 7,306,764 B2 | 12/2007 | Mody |
| 7,355,090 B2 | 4/2008 | Ales, III et al. |
| 7,394,391 B2 | 7/2008 | Long |
| 7,477,156 B2 | 1/2009 | Long et al. |
| 7,489,252 B2 | 2/2009 | Long et al. |
| 7,492,270 B2 | 2/2009 | Veerasamy |
| 7,498,478 B2 | 3/2009 | Long et al. |
| 7,642,396 B2 | 1/2010 | Ales, III et al. |
| 7,649,125 B2 | 1/2010 | Ales, III et al. |
| 7,731,665 B2 | 6/2010 | Lee et al. |
| 7,812,731 B2 | 10/2010 | Bunza et al. |
| 7,833,177 B2 | 11/2010 | Long et al. |
| 8,098,900 B2 | 1/2012 | Determan et al. |
| 8,134,042 B2 | 3/2012 | Song et al. |
| 8,222,476 B2 | 7/2012 | Song et al. |
| 8,274,393 B2 | 9/2012 | Ales et al. |
| 8,557,894 B2 | 10/2013 | Song et al. |
| 8,795,138 B1 | 8/2014 | Yeh et al. |
| 8,866,624 B2 | 10/2014 | Ales, III et al. |
| 9,138,354 B2 | 9/2015 | Nhan et al. |
| 9,408,757 B2 | 8/2016 | Elfstroem et al. |
| 2001/0044588 A1 | 11/2001 | Mault |
| 2001/0049513 A1* | 12/2001 | Neading ............ A61F 13/42 604/361 |
| 2002/0026164 A1 | 2/2002 | Camarero et al. |
| 2002/0145526 A1 | 10/2002 | Friedman et al. |
| 2003/0028165 A1 | 2/2003 | Curro et al. |
| 2003/0060789 A1 | 3/2003 | Shapira et al. |
| 2003/0125682 A1 | 7/2003 | Olson et al. |
| 2003/0171729 A1 | 9/2003 | Kaun et al. |
| 2004/0089058 A1 | 5/2004 | De Haan et al. |
| 2004/0102750 A1 | 5/2004 | Jameson |
| 2004/0106202 A1 | 6/2004 | Zainiev et al. |
| 2004/0111045 A1 | 6/2004 | Sullivan et al. |
| 2004/0113801 A1 | 6/2004 | Gustafson et al. |
| 2004/0118540 A1 | 6/2004 | Garnier et al. |
| 2004/0131651 A1 | 7/2004 | Panero et al. |
| 2004/0138546 A1 | 7/2004 | Reho et al. |
| 2004/0138723 A1 | 7/2004 | Malick et al. |
| 2004/0140897 A1 | 7/2004 | Fabre et al. |
| 2004/0147888 A1 | 7/2004 | Huang et al. |
| 2004/0172000 A1 | 9/2004 | Roe et al. |
| 2004/0207530 A1 | 10/2004 | Nielsen |
| 2004/0220538 A1 | 11/2004 | Panopoulos |
| 2004/0236302 A1 | 11/2004 | Wilhelm et al. |
| 2005/0046578 A1 | 3/2005 | Pires |
| 2005/0054255 A1 | 3/2005 | Morman et al. |
| 2005/0059941 A1 | 3/2005 | Baldwin et al. |
| 2005/0120919 A1 | 6/2005 | Davies-Smith et al. |
| 2005/0136772 A1 | 6/2005 | Chen et al. |
| 2005/0137542 A1 | 6/2005 | Underhill et al. |
| 2005/0156744 A1 | 7/2005 | Pires |
| 2005/0195085 A1 | 9/2005 | Cretu-Petra |
| 2005/0245839 A1 | 11/2005 | Stivoric et al. |
| 2005/0251036 A1 | 11/2005 | Abuhamad |
| 2005/0274470 A1 | 12/2005 | Shannon et al. |
| 2005/0287356 A1 | 12/2005 | Li et al. |
| 2006/0069360 A1 | 3/2006 | Long et al. |
| 2006/0069362 A1 | 3/2006 | Odorzynski et al. |
| 2006/0174693 A1 | 8/2006 | Chen et al. |
| 2006/0229577 A1 | 10/2006 | Roe et al. |
| 2006/0229578 A1 | 10/2006 | Roe et al. |
| 2006/0258916 A1 | 11/2006 | Pietersen |
| 2007/0017413 A1 | 1/2007 | Kwan et al. |
| 2007/0048709 A1 | 3/2007 | Ales, III et al. |
| 2007/0142797 A1 | 6/2007 | Long et al. |
| 2007/0142799 A1 | 6/2007 | Ales et al. |
| 2007/0156106 A1 | 7/2007 | Klofta et al. |
| 2007/0252712 A1 | 11/2007 | Allen et al. |
| 2007/0270774 A1 | 11/2007 | Bergman et al. |
| 2007/0273504 A1 | 11/2007 | Tran |
| 2008/0021423 A1 | 1/2008 | Klofta et al. |
| 2008/0041792 A1 | 2/2008 | Crnkovich et al. |
| 2008/0048786 A1 | 2/2008 | Feldkamp et al. |
| 2008/0054408 A1 | 3/2008 | Tippey et al. |
| 2008/0058745 A1 | 3/2008 | Long et al. |
| 2008/0076313 A1 | 3/2008 | Uitenbroek et al. |
| 2008/0077040 A1 | 3/2008 | Ales et al. |
| 2008/0077042 A1 | 3/2008 | Feldkamp et al. |
| 2008/0082151 A1 | 4/2008 | Quincy et al. |
| 2008/0129519 A1 | 6/2008 | Gabriel |
| 2008/0132859 A1 | 6/2008 | Pires |
| 2008/0145947 A1 | 6/2008 | Boga et al. |
| 2008/0147030 A1 | 6/2008 | Nhan et al. |
| 2008/0147031 A1 | 6/2008 | Long et al. |
| 2008/0167535 A1 | 7/2008 | Stivoric et al. |
| 2008/0168829 A1 | 7/2008 | Paez |
| 2008/0243099 A1 | 10/2008 | Tippey et al. |
| 2008/0262376 A1 | 10/2008 | Price |
| 2008/0266122 A1 | 10/2008 | Ales et al. |
| 2008/0278336 A1 | 11/2008 | Ortega et al. |
| 2008/0278337 A1 | 11/2008 | Huang et al. |
| 2008/0284608 A1 | 11/2008 | Long |

(56) References Cited

U.S. PATENT DOCUMENTS

| | | |
|---|---|---|
| 2008/0287747 A1 | 11/2008 | Mestrovic et al. |
| 2008/0306461 A1 | 12/2008 | Jan |
| 2009/0005748 A1 | 1/2009 | Ales et al. |
| 2009/0036012 A1 | 2/2009 | Nhan et al. |
| 2009/0036850 A1 | 2/2009 | Nhan et al. |
| 2009/0062756 A1 | 3/2009 | Magic et al. |
| 2009/0062757 A1 | 3/2009 | Long et al. |
| 2009/0157024 A1 | 6/2009 | Song |
| 2009/0194532 A1 | 8/2009 | Yang et al. |
| 2009/0275908 A1 | 11/2009 | Song |
| 2009/0326417 A1 | 12/2009 | Ales, III et al. |
| 2010/0015658 A1 | 1/2010 | Yang et al. |
| 2010/0152688 A1* | 6/2010 | Handwerker ........... A61F 13/42 604/361 |
| 2010/0168694 A1 | 7/2010 | Gakhar et al. |
| 2010/0215542 A1 | 8/2010 | Hill et al. |
| 2010/0277324 A1 | 11/2010 | Yeh |
| 2011/0144602 A1 | 6/2011 | Long et al. |
| 2012/0053423 A1 | 3/2012 | Kenalty et al. |
| 2012/0116337 A1* | 5/2012 | Ales ........................ A61F 13/42 604/361 |
| 2012/0157947 A1 | 6/2012 | Nhan et al. |
| 2012/0216607 A1 | 8/2012 | Sjoeholm et al. |
| 2012/0220969 A1* | 8/2012 | Jang ........................ A61F 13/42 604/361 |
| 2012/0268278 A1 | 10/2012 | Lewis et al. |
| 2013/0324955 A1 | 12/2013 | Wong et al. |
| 2014/0121473 A1 | 5/2014 | Banet et al. |
| 2014/0155850 A1 | 6/2014 | Shah et al. |
| 2014/0188063 A1* | 7/2014 | Nhan ................ A61F 13/00055 604/361 |
| 2014/0232516 A1 | 8/2014 | Stivoric et al. |
| 2014/0327546 A1 | 11/2014 | Carney et al. |
| 2015/0320609 A1 | 11/2015 | Thoen |
| 2016/0078176 A1 | 3/2016 | Ranta et al. |
| 2016/0120453 A1 | 5/2016 | Pop et al. |

FOREIGN PATENT DOCUMENTS

| | | |
|---|---|---|
| DE | 19918681 A1 | 10/2000 |
| DE | 19937779 A1 | 2/2001 |
| DE | 19939902 A1 | 3/2001 |
| EP | 0446821 A2 | 9/1991 |
| EP | 0810847 B1 | 8/2000 |
| EP | 1424918 B1 | 11/2005 |
| GB | 2321990 A | 8/1998 |
| JP | 09-033468 A | 2/1997 |
| JP | 09-187431 A | 7/1997 |
| JP | 09-220259 A | 8/1997 |
| JP | 09-290001 A | 11/1997 |
| JP | 10-314202 A | 12/1998 |
| JP | 2001-318067 A | 11/2001 |
| JP | 2002-071584 A | 3/2002 |
| JP | 2002-153497 A | 5/2002 |
| JP | 2005-013244 A | 1/2005 |
| JP | 2006-043389 A | 2/2006 |
| JP | 2011-022121 A | 2/2011 |
| KR | 10-0484478 B1 | 4/2005 |
| KR | 10-2009-0081886 A | 7/2009 |
| WO | WO 1991/019471 A1 | 12/1991 |
| WO | WO 1995/016425 A2 | 6/1995 |
| WO | WO 1999/020216 A1 | 4/1999 |
| WO | WO 2000/000082 A1 | 1/2000 |
| WO | WO 2000/037009 A2 | 6/2000 |
| WO | WO 2000/076443 A1 | 12/2000 |
| WO | WO 2001/012150 A1 | 2/2001 |
| WO | WO 2001/095845 A1 | 12/2001 |
| WO | WO 2003/007997 A2 | 1/2003 |
| WO | WO 2003/051254 A2 | 6/2003 |
| WO | WO 2004/021944 A1 | 3/2004 |
| WO | WO 2004/028429 A1 | 4/2004 |
| WO | WO 2004/100763 A2 | 11/2004 |
| WO | WO 2005/106465 A1 | 11/2005 |
| WO | WO 2006/073096 A1 | 7/2006 |
| WO | WO 2007/087674 A1 | 8/2007 |
| WO | WO 2010/043368 A1 | 4/2010 |
| WO | WO 2010/123425 A1 | 10/2010 |
| WO | WO 2016/138331 A1 | 9/2016 |

* cited by examiner

ABSORBENT ARTICLE LEAKAGE ASSESSMENT SYSTEM

BACKGROUND

Absorbent articles such as diapers, training pants, incontinence products, feminine hygiene products, swim undergarments, and the like, conventionally include a liquid permeable body-side liner, a liquid impermeable outer cover, and an absorbent structure. The absorbent structure is typically located between the outer cover and the liner for taking in and retaining liquids (e.g., urine) exuded by the wearer. The absorbent structure can be made of, for instance, superabsorbent particles. Due to a variety of potential reasons, some absorbent articles will leak urine or other body fluids, particularly in an overnight setting. These potential reasons can include body position, amount of urine already in the product, body geometries of wearers, and other potential reasons. It is typically difficult to determine where, when, and how an absorbent article has leaked urine or other bodily fluids, especially when the absorbent article is being worn by a newborn or other very young wearers, and especially when the article is worn overnight.

Various types of moisture or wetness indicators have been suggested for use in absorbent articles. The wetness indicators include various passive indicators such as indicator strips, printing, or other devices within each absorbent article. Wetness indicators can also include alarm devices that are designed to assist parents or attendants in identifying a wet absorbent article condition early on. The devices can produce an audible, tactile, electromagnetic, or visual signal. Many of these devices rely on electronics, including conductive elements within each absorbent article that can increase the expense of the absorbent article. None of these is designed to indicate leakage from the absorbent article. Wetness-sensing bed pads are also available to indicate when urination has reached bedding, for example.

In view of the above, a need currently exists for an absorbent article leakage assessment system that can be used to determine under what circumstances an absorbent article leaks.

SUMMARY

To understand the fundamental problem of overnight leakage, a determination of baby position, urination occurrence, leakage timing, and leakage location is required. The present inventors undertook intensive research and development efforts with respect to improving absorbent articles, particularly in providing an absorbent article leakage assessment system that can be used to determine under what circumstances an absorbent article leaks. Technology that can be implemented without altering absorbent article construction is preferred.

The present disclosure is generally directed to a leakage assessment system for use with an absorbent article having an outer surface, the system including a computer and a signaling device adapted to be used in conjunction with the absorbent article, the signaling device adapted to sense wetness in the absorbent article, wherein the signaling device is in electronic communication with the computer. The system also includes a wetness detection mat in electronic communication with the computer, and an image capture device configured to continuously detect an absorbent article wearer position, wherein the image capture device is in electronic communication with the computer, wherein the computer is configured to electronically record wetness incidents using the signaling device, the wetness detection mat, and the wearer position captured by the image capture device.

The present disclosure is also directed to a method for assessing leakage from an absorbent article in use by a wearer, the method including placing the absorbent article on the wearer, the absorbent article comprising wetness detection indicia and a signaling device; positioning the wearer on a bed or other surface; and disposing a wetness detection mat between the absorbent article and the bed. The method also includes using a camera, continuously detecting the position of the wearer; electronically recording wetness incidents using the signaling device, the wetness detection mat, and wearer position; and viewing the wetness detection indicia to detect where leakage occurred.

Other features and aspects of the present disclosure are discussed in greater detail herein.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
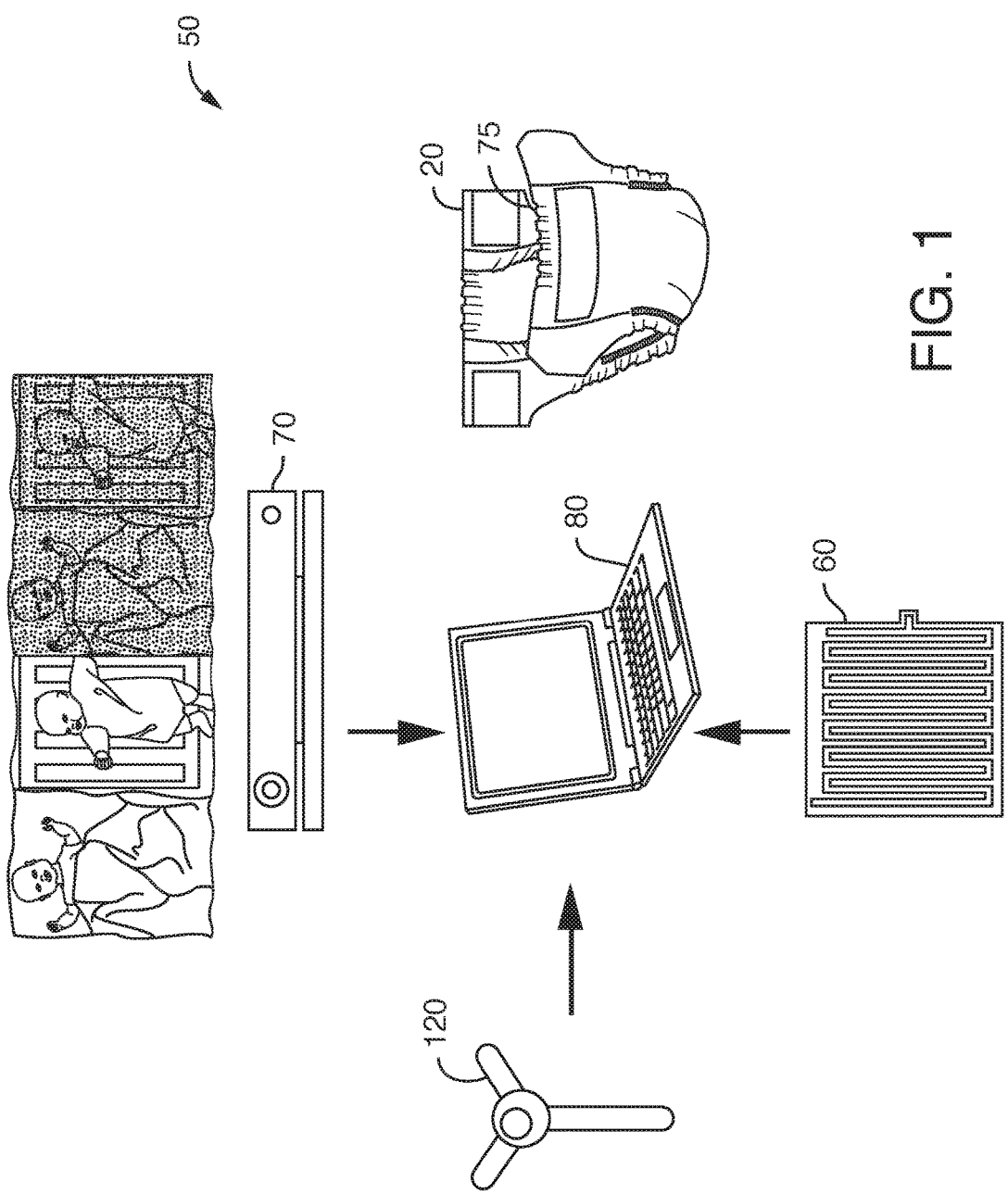
FIG. 1 is a schematic view of a leakage assessment system of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects only, and is not intended as limiting the broader aspects of the present disclosure.

The present disclosure is generally directed to a leakage assessment system 50 for absorbent articles that indicate to researchers when a body fluid has insulted and then leaked from the absorbent article. The signaling systems of the present disclosure, on the other hand, can sense the presence of a body fluid from an exterior surface of the article that can greatly simplify the incorporation of the signaling system into the article.

Figure 2:
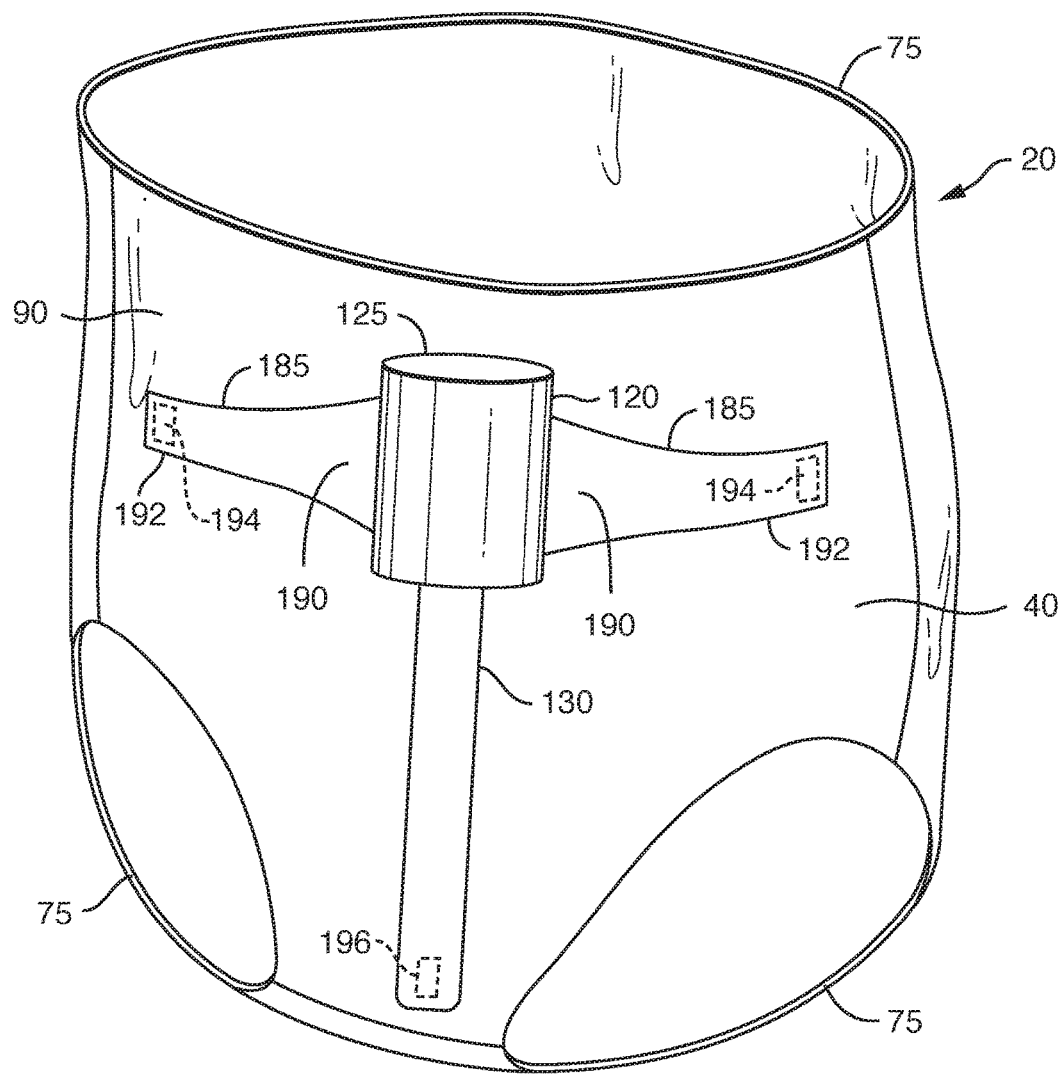
FIG. 2 is a perspective view of a signaling device and an absorbent article of the present disclosure to be used in association with the leakage assessment system of FIG. 1.

In accordance with the present disclosure, the signaling system can have various configurations and designs. Referring to FIG. 2, for exemplary purposes, an absorbent article 20 that can be used in conjunction with signaling systems of the present disclosure is shown. The absorbent article 20 can be disposable or not. It is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like, without departing from the scope of the present disclosure.

By way of illustration only, various materials and methods for constructing absorbent articles such as the absorbent article 20 of the various aspects of the present disclosure are disclosed in PCT Patent Disclosure WO 00/037009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

The illustrated absorbent article 20 includes an outer cover 40 and a waist region 90.

As illustrated in FIG. 1, a leakage assessment system 50 of the present disclosure is configured for use in conjunction with an absorbent article. The leakage assessment system 50 includes a signaling device 120 for use in conjunction with the absorbent article 20, a wetness detection mat 60 to detect leakage from the absorbent article 20, and an image capture device 70 to continuously detect the position of a wearer of the absorbent article 20. In addition, the leakage assessment system 50 can include wetness detection indicia 75 on the absorbent article 20 itself to help determine the point of leakage. Finally, the leakage assessment system 50 includes a computer 80 to receive, interpret, and coordinate signals from the signaling device, the wetness detection mat, and the image capture device 70.

The signaling device 120 is adapted to be used in conjunction with the absorbent article 20 to sense wetness, such as from urine, feces, or other body exudates, within the absorbent article 20. It is important that any signaling device 120 used should not alter the function of the absorbent article 20 or at least should have a minimal impact on the function of the absorbent article 20. The leakage assessment system 50 is intended to identify opportunities to improve the absorbent article 20, so the best results will be obtained if the absorbent article 20 functions as it normally would if it were not being observed. The signaling device 120 detects when a urination event starts and broadcasts, for example, a Bluetooth wireless signal to the computer 80. The signaling device 120 can also detect multiple insults. The signaling device 120 can be configured to detect and indicate in addition to wetness dry time, time in wet product, number of insults to single diaper, fullness detection through algorithms, and fullness detection through sensing.

The reusable signaling device 120 is adapted to sense wetness without the use of conductors within the absorbent article 20. Suitable wetness sensing technologies include capacitance-based sensors such as those described in U.S. patent Ser. No. 12/648,645 (now U.S. Pat. No. 8,866,624), inductance-based sensors such as those described in U.S. patent Ser. No. 11/983,970 (now U.S. Pat. No. 8,207,394), and infrared reflectance-based sensors such as those described in U.S. patent Ser. No. 12/636,888, each of which is incorporated herein by reference to the extent it does not conflict herewith. Any other suitable sensor technology can be employed.

Sensors such as those described herein are further described, for instance, in U.S. Patent Disclosure Publication No. 2008/0048786 (now U.S. Pat. No. 8,725,245), which is incorporated herein by reference to the extent it does not conflict herewith.

Referring to FIG. 2, the signaling device 120 can include a housing 125. The housing 125 can be designed so that the signaling device 120 minimizes any discomfort when worn. In addition to being comfortable when attached to an absorbent article 20, however, the signaling device 120 must also be durable. Based upon anthropomorphic modeling, signaling devices 120 made in accordance with the present disclosure are produced with dimensions that fall within a set of desirable ranges. In addition, the signaling device 120 can also include radii on the corners of the signaling device 120 that are constrained by a set of desirable ranges to ensure that the corners do not impinge, scratch, or poke the body's surface.

In this aspect, the signaling device 120 can include internal components. The internal components, for instance, can include a battery and can be configured to generate an audible signal, a tactile signal, an electromagnetic signal, a wireless signal, a visual signal, any other suitable signal, or any combination of these. The housing 125 in this aspect can have a rectangular shape, such as a square shape, with rounded corners, or the housing 125 can be circular, ovoid, or any other suitable shape. Housings 125 suitable for use in the signaling device 120 described herein include those further described, for instance, in U.S. patent Ser. No. 11/848,714, which is incorporated herein by reference to the extent it does not conflict herewith.

As illustrated in FIG. 2, the signaling device 120 can also include a flexible sensor band 130 extending from the housing 125. The flexible sensor band 130 can be a flexible plastic film including an array of capacitive-based sensing elements. The sensing elements can take form of two planar electrodes making an open-face virtual capacitor. The flexible sensor band 130 can be made by etching from copper sheets laminated onto a flexible and non-conductive substrate. Such flexible and non-conductive substrates include polyimide, polyester, and any other suitable material. An example of such material is KAPTON films made by E. I. du Pont de Nemours and Company of Wilmington, Del. The etching method is widely used to make printed circuit boards in the electronic industry. Other methods of making a flexible printed circuit board include silk screen printing, gravure printing, and flexographic printing. The conductive material forming open face capacitors is made with conductive materials such as copper, silver, or carbon black. The flexible sensing band 130 can be electrically connected to the signaling device 120 by a ZIF connector or any other suitable connector.

In one aspect of the present disclosure, the signaling device 120 includes a capacitive sensor that is adapted to detect the presence of a body exudate in the absorbent article 20. A noninvasive capacitive-based touch sensor can be used to determine the permittivity of material near the sensing element. The sensing element can take the form of an open face virtual capacitor that, when energized, creates an electric field.

The capacitive sensor includes a capacitive touch sensing means. The capacitive touch sensing means can include two electrodes creating an electrostatic field that extends beyond the face of the antenna or electrodes, in this case beyond the face of the signaling device 120. Conductive substances such as body exudates in the absorbent article 20 act as dielectrics that change field dynamics, causing a load on the system. This load amount can be read as merely the presence or the extent of the presence of moisture, for example. Construction and the power applied to the electrodes can control the extent to which the field extends and the frequency of the power can be adjusted to fine tune selectivity to certain dielectrics.

For example, a noninvasive, capacitive-based touch sensor can be used to determine the permeability of material near the sensing element. The sensing element can take a form of an inter-digitized electrode forming an open-face virtual capacitor. Similar technology has been used to determine moisture content in soil and in touch sensors such as key pads, thumbwheels, etc. As described herein, this technology can be applied to detect wetness in an absorbent article from outside the outer cover. Key challenges, however, with such a capacitive touch sensing system are managing the penetration depth of the electric field and the ability of the system to detect a small amount of wetness from outside the outer cover. Such challenges can be resolved through signal conditioning and developing algorithms to ignore environmental interferences, as described below.

Sensor design is important in determining the sensitivity of the capacitive sensor to detect wetness in the absorbent article 20. Some of the important parameters include the diameter of the capacitor pad, for example from 5 to 15 mm, the number of capacitors in one array, for example from 1 to 10, and the spacing between the capacitor and the ground plane, for example from 1 mm to 2.5 mm. A ground plane can be positioned at the back of the sensor to prevent interference from the back side of the sensor. There are several array geometries that can be used for a capacitive sensing array.

In various aspects of the present disclosure, different methods can be used in constructing a capacitive sensor. In a first method, the sensor can be viewed as a constant capacitance sensor because the sensor size and distance to the ground plane cannot change. Any parasitic capacitance, either trace capacitance, IC capacitance, or ADC capacitance, can be said to be constant. When the sensor is in open air, it is a parallel plate capacitor, with one side seeing electric fields normal to the ground plane below it. There is slight fringing to the adjacent ground plane.

When an absorbent article 20 or any material with a higher dielectric than air is present on the top of the sensor, the fringing fields present when air was only present now spread into the higher dielectric material and have a better path to a lower potential or ground. This increases the capacitance and can be detected using the ADC. When water is present in the absorbent article 20, the dielectric constant now increases much more than when an absorbent article 20 or other dielectric was present. Water has a dielectric greater than 50 and now provides a better path for the electric fields to a lower potential or ground.

One example of a system design for this method includes a microcontroller made by Microchip Inc., part number PIC24FJ128GA106, which has a dedicated charge time measurement unit (CTMU). The CTMU is a module add-on to the microcontroller that can be used directly to detect changes in capacitance. In this system design, an array of capacitor sensors are attached to the A/D inputs of the Microchip PIC 24FJ series microcontroller and used to compute the changes in capacitance as the dielectric changes in presence of wetness.

In a second method, changes are detected in the resonant frequency of an LC circuit. As the capacitance value of the resonator circuit changes the frequency of the oscillating frequency of the resonator changes, this can be detected by a frequency-to-voltage (F/V) converting chip such as TC 9400 made by Microchip Technologies Inc. of Chandler, Ariz. U.S.A. The F/V converter produces a voltage used by a microcontroller. When a voltage setpoint is reached, as determined by the microcontroller, an alarm signal is generated.

A third method measures the time taken to discharge a capacitor. A resistor-capacitor (RC) circuit has a characteristic discharge curve dependent on the capacitor under test. A system capable of measuring this time constant of this discharge curve can be used to detect the changes in the capacitance. In other words, as the capacitance of the system is different with an insulted absorbent article as compared to a dry absorbent article, the discharge curve will be different as well. In use, an open face virtual capacitor is manufactured using an RC circuit including a step function/pulse generator. The discharge time of the system capacitance is detected and processed using a digital signal processing (DSP) algorithm in a microcontroller. When insult conditions are reached, as determined by the microcontroller, an alarm signal is generated as further described herein.

As illustrated in FIG. 2, the signaling device 120 includes flexible arms 185 having proximal and distal ends 190, 192. Each distal end 192 can include an attachment means 194. The flexible arms 185 can be attachable to the outer cover 40 using adhesives, cohesives, mechanical fasteners such as hook material, or any other suitable attachment means. The flexible sensor band 130, if present, can also include an attachment means 196 such that the flexible sensor band 130 is attachable to the outer cover 40. The flexible sensor band 130 can be attachable to the outer cover 40 using adhesives, cohesives, mechanical fasteners such as hook material, or any other suitable attachment means. Once the signaling device 120 is attached to the outer cover 40, the signaling device 120 is then ready to sense wetness within the article 20. The flexible arms 185 and the flexible sensor band 130 can be manufactured from woven material or non-woven material such as SMS, spun-bond, film such as polypropylene, rubber, other elastomeric material, or from any other suitable material, either alone or laminated to a non-woven.

In an alternate aspect of the present disclosure, the flexible arms 185, the flexible band 130, and the signaling device 120 can be formed together as one unit of injection-molded plastic. The attachment means 194, 196 can be an adhesive, a cohesive, hook material, or any other suitable attachment material.

Various attachment mechanisms include those disclosed in co-pending and co-assigned U.S. Patent Disclosure Publication No. 2007/0142797 to Long, et al. and entitled "Garments With Easy-To-Use Signaling Device"; U.S. Patent Disclosure Publication No. 2006/0244614 to Long and entitled "Connection Mechanisms" (now U.S. Pat. No. 7,394,391); and U.S. Patent Disclosure Publication No. 2007/0024457 to Long, et al. and entitled "Connection Mechanisms In Absorbent Articles For Body Fluid Signaling Devices" (now U.S. Pat. No. 7,477,156), which are incorporated herein by reference to the extent they are consistent (i.e., not in conflict) herewith.

The signaling device 120 can emit any suitable signal to indicate to the user that the absorbent article 20 has been insulted. The signal, for instance, can include an audible signal, a tactile signal, an electromagnetic signal, a wireless signal, a visual signal, any other suitable signal, or any combination of these. The audible signal, for instance, can be as simple as a beep or can include a musical tune. In still another aspect, the signaling device can emit a wireless signal that communicates with a remote device such as a computer 80.

Further aspects of the signaling device 120 can be found in U.S. patent Ser. No. 12/347,539, entitled "Remote Detection Systems For Absorbent Articles" (now U.S. Pat. No. 8,274,393), which is incorporated herein by reference to the extent it does not conflict herewith.

Referring to FIG. 1, the leakage assessment system 50 also includes a wetness detection mat 60. The wetness detection mat 60 can be any suitable mat including those commonly known in the art. The wetness detection mat 60 is also in electronic communication with the computer 80 and sends a signal when the wetness detection mat 60 detects wetness such as that having leaked from the absorbent article 20. Currently-available wetness detection mats 60 include the WET CALL bed-side alarm sensor pad, the pad available in the DRY-ME bed-mat treatment system, the VIGILANT bed wetting urine alarm sensor pad mat kit, and the CHUMMIE INTELLIFLEX sensor. In one aspect, the wetness detection mat 60 can communicate with the computer 80 using a NATIONAL INSTRUMENTS USB-6001 Multifunction DAQ to interface the wetness detection mat 60 to a USB port. In other aspects, suitable devices are available from other manufacturers including Measurement Computing. In an alternative aspect, the wetness detection mat 60 can interface to a USB port by tapping into the alarm module of the wetness detection mat 60 by monitoring Alarm and Reset signals with a device such as the SPARK-FUN USB to Serial Breakout—FT232RL.

The leakage assessment system 50 also includes an image capture device 70 such as a still camera, a video camera, a "web"-type camera, or any other suitable image capture device 70. In a particular aspect, the image capture device 70 is a KINECT V2.0 system, which is an off-the-shelf imaging sensor commonly associated with gaming systems and that is available from Microsoft Corp. The KINECT system requires USB 3.0 and Windows 8.0 or higher. The KINECT system uses a combination of color and infrared (IR) sensors to create a multiple image data stream that can be processed to extract high resolution 3D-type images. Software libraries designed for the KINECT system present the data in various formats. For the leakage assessment system 50 described herein, the sensor system of the KINECT system is used to detect body position during insult, at intervals after that, and finally at leak detection. The imaging capture device 70 has another advantage in that the data can be present without providing a clear indication of the subject's identity.

The leakage assessment system 50 also includes wetness detection indicia 75 on the absorbent article 20 itself to help determine the point of leakage. For example, the perimeter of the absorbent article 20 (waist and leg openings in the case of a wearable absorbent article 20) can be coated with color changing ink (urine activated) such that a visual inspection of the absorbent article 20 will determine where in the absorbent article 20 the leakage occurred. Other wetness detection indicia 75 contemplated herein include water-based color washing inks and color changing adhesives.

Finally, the leakage assessment system 50 includes a computer 80 configured to electronically record wetness and leakage incidents using the signaling device 120, the wetness detection mat 60, and the wearer position captured by the image capture device 70. A commonly-available personal computer or laptop 80 is used to coordinate the sensor and output function. The computer 80 receives data and triggers from the signaling device 120, which can use Bluetooth LE to communicate. The computer 80 also receives data and triggers from the wetness detection mat 60, which can interface with the serial port(s) of the computer 80. Finally, the computer 80 also receives data and triggers from the imaging capture device 70 (e.g., a KINECT V2.0 system), which can require at least a USB 3.0 interface to communicate. A program on the computer 80 monitors the ports and other inputs and captures for storage system images from the imaging capture device 70 at appropriate times. The leakage assessment system 50 can be monitored remotely for both data collection and to insure the system is functioning properly.

Understanding the risks of overnight leakage can be very important to the manufacturer of absorbent articles, and the results of such understanding can be very important to an absorbent article consumer. Components of this understanding include body position, when urination occurs, whether a leak occurs upon urination, where in the absorbent article 20 that leak emerges, and in which body positions the absorbent article 20 does not leak. Heretofore there was no reliable methodology to gather all of this information, which means that absorbent article manufacturers have not been sure that their absorbent articles are designed to meet criteria that minimize leakage rates and costs. The leakage assessment system 50 described herein can be used to collect overnight leakage and position data for an absorbent article 20 in use. The leakage assessment system 50 provides key metrics on overnight leakage in that it allows for the collection of quantitative data on insult time, body position, time of leakage, and position of leakage from an absorbent article while maintaining the anonymity of the wearer during placement. Other measurements that may aid in understanding the fundamental problem of overnight leakage (e.g., volume of liquid expelled in any urination) can also be incorporated into the leakage assessment system 50. Although the leakage assessment system 50 is particularly useful in understanding the fundamental problem of overnight leakage, the leakage assessment system 50 can be used to understand the fundamental problem of leakage during other conditions, such as daytime conditions, particularly for immobile users of absorbent products.

In use, the leakage assessment system 50 can provide data related to overnight wear of an absorbent article 20 and any associated leakage event. Just prior to bed time or nap time, an absorbent article 20 is placed on the wearer. The absorbent article 20 includes wetness detection indicia 75 at the leg and waist openings. A wetness detection mat 60 is placed on or under the sheets of a bed and is then connected to the computer 80. An image capture device 70 (e.g., a KINECT system) is placed adjacent to the bed using a stand as appropriate to insure safe placement, and then is connected to the computer 80, such as by using a USB cable. A signaling device 120 is attached to the outer cover 40 of the absorbent article 20. Finally, the wearer is placed on the bed or other surface above the wetness detection mat 60 and within range of the image capture device 70. The computer is set to receive, coordinate, and interpret data from the signaling device 120, the wetness detection mat 60, and the image capture device 70.

After the sleep period, the computer 80 is checked for the status of insult to and leakage from the absorbent article 20. If an insult has occurred as indicated by the signaling device 120, but no leak was detected by the wetness detection mat 60, then the absorbent article 20 has performed as designed. If an insult has occurred as indicated by the signaling device 120, and a leak was detected by the wetness detection mat 60, then the wetness detection indicia 75 of the absorbent article 20 is examined to determine where the leak occurred. From information provided by the signaling device 120, the wetness detection mat 60, the image capture device 70, and the wetness detection indicia 75, it can be determined when an insult occurred, when and where a leakage occurred, and the position of the wearer when the leakage occurred. This provides valuable input to a manufacturer to help determine how to design absorbent articles to minimize leakage.

In a first particular aspect, a leakage assessment system for use with an absorbent article having an outer surface includes a computer and a signaling device adapted to be used in conjunction with the absorbent article, the signaling device adapted to sense wetness in the absorbent article, wherein the signaling device is in electronic communication with the computer. The leakage assessment system also includes a wetness detection mat in electronic communication with the computer, and an image capture device configured to continuously detect an absorbent article wearer position, wherein the image capture device is in electronic communication with the computer, wherein the computer is configured to electronically record wetness incidents using the signaling device, the wetness detection mat, and the wearer position captured by the image capture device.

A second particular aspect includes the first particular aspect, wherein the absorbent article includes edges, and wherein the absorbent article edges include wetness detection indicia.

A third particular aspect includes the first or second aspect, wherein the wetness detection indicia include a color-changing ink.

A fourth particular aspect includes one or more of aspects 1-3, wherein the signaling device is configured to detect wetness using capacitance.

A fifth particular aspect includes one or more of aspects 1-4, wherein the signaling device is configured to detect wetness using inductance.

A sixth particular aspect includes one or more of aspects 1-5, wherein the signaling device is configured to detect wetness using infrared reflectance.

A seventh particular aspect includes one or more of aspects 1-6, wherein the signaling device is adapted to be attached to the outer surface of the absorbent article.

An eighth particular aspect includes one or more of aspects 1-7, wherein the signaling device includes a mechanical attachment means.

A ninth particular aspect includes one or more of aspects 1-8, wherein the mechanical attachment means is hook material.

A tenth particular aspect includes one or more of aspects 1-9, wherein the signaling device includes an adhesive attachment means.

An eleventh particular aspect includes one or more of aspects 1-10, wherein the signaling device includes a housing and a flexible sensor band extending from the housing.

A twelfth particular aspect includes one or more of aspects 1-11, wherein the image capture device is a KINECT imaging sensor.

A thirteenth particular aspect includes one or more of aspects 1-12, wherein the wetness detection mat is configured to electronically detect wetness.

In a fourteenth particular aspect, a method for assessing leakage from an absorbent article in use by a wearer includes placing the absorbent article on the wearer, the absorbent article comprising wetness detection indicia and a signaling device; positioning the wearer on a bed or other surface; and disposing a wetness detection mat between the absorbent article and the bed. The method also includes using a camera, continuously detecting the position of the wearer; electronically recording wetness incidents using the signaling device, the wetness detection mat, and wearer position; and viewing the wetness detection indicia to detect where leakage occurred.

A fifteenth particular aspect includes the fourteenth particular aspect, wherein the wetness detection indicia include a color-changing ink.

A sixteenth particular aspect includes the fourteenth or fifteenth aspect, wherein the signaling device is configured to detect wetness using capacitance.

A seventeenth particular aspect includes one or more of aspects 14-16, wherein the absorbent article includes an outer surface, and wherein the signaling device is adapted to be attached to the outer surface of the absorbent article.

An eighteenth particular aspect includes one or more of aspects 14-17, wherein the signaling device includes a housing and a flexible sensor band extending from the housing.

A nineteenth particular aspect includes one or more of aspects 14-18, wherein the image capture device is a KINECT imaging sensor.

In a twentieth particular aspect, a leakage assessment system for use with an absorbent article having an outer surface includes a computer and a signaling device adapted to be used in conjunction with the absorbent article, the signaling device adapted to sense wetness in the absorbent article using capacitance, wherein the signaling device is in electronic communication with the computer, and wherein the signaling device is adapted to be attached to the outer surface of the absorbent article. The system also includes a wetness detection mat in electronic communication with the computer, wherein the wetness detection mat is configured to electronically detect wetness; and an image capture device configured to continuously detect an absorbent article wearer position, wherein the image capture device is in electronic communication with the computer, wherein the computer is configured to electronically record wetness incidents using the signaling device, the wetness detection mat, and the wearer position captured by the image capture device.

These and other modifications and variations to the present disclosure can be practiced by those of ordinary skill in the art, without departing from the spirit and scope of the present disclosure, which is more particularly set forth in the appended claims. In addition, it should be understood that elements of the various aspects can be interchanged both in whole and in part. Furthermore, those of ordinary skill in the art will appreciate that the foregoing description is by way of example only, and is not intended to limit the disclosure so further described in such appended claims.

What is claimed:

1. A leakage assessment system for use with an absorbent article having a body-side liner, an outer cover providing an outer surface, and an absorbent structure located between the outer cover and the body-side liner, the system comprising:
   a computer;
   a signaling device adapted to be used in conjunction with the absorbent article, the signaling device adapted to sense wetness in the absorbent article, wherein the signaling device is in electronic communication with the computer;
   a wetness detection mat in electronic communication with the computer, the wetness detection mat configured to detect leakage from the absorbent article of urine or other bodily fluid leaking out of the absorbent article; and
   an image capture device configured to continuously detect an absorbent article wearer position, wherein the image capture device is in electronic communication with the computer, wherein the computer is configured to electronically record wetness incidents using the signaling device, the wetness detection mat, and the wearer position captured by the image capture device.

2. The system of claim 1, wherein the absorbent article includes edges, and wherein the absorbent article edges include wetness detection indicia.

3. The system of claim 2, wherein the wetness detection indicia include a color-changing ink.

4. The system of claim 1, wherein the signaling device is configured to detect wetness using capacitance.

5. The system of claim 1, wherein the signaling device is configured to detect wetness using inductance.

6. The system of claim 1, wherein the signaling device is configured to detect wetness using infrared reflectance.

7. The system of claim 1, wherein the signaling device is adapted to be attached to the outer surface of the absorbent article.

8. The system of claim 7, wherein the signaling device includes a mechanical attachment means.

9. The system of claim 8, wherein the mechanical attachment means is hook material.

10. The system of claim 7, wherein the signaling device includes an adhesive attachment means.

11. The system of claim 1, wherein the signaling device includes a housing and a flexible sensor band extending from the housing.

12. The system of claim 1, wherein the image capture device is an imaging sensor comprising color and infrared sensors.

13. The system of claim 1, wherein the wetness detection mat is configured to electronically detect wetness.

14. A method for assessing leakage from an absorbent article in use by a wearer, the method comprising:
    placing the absorbent article on the wearer, the absorbent article comprising a body-side liner, an outer cover providing an outer surface, and an absorbent structure located between the outer cover and the body-side liner, the absorbent article further comprising wetness detection indicia and a signaling device adapted to sense wetness in the absorbent article;
    positioning the wearer on a bed or other surface;
    disposing a wetness detection mat between the absorbent article and the bed, the wetness detection mat configured to detect leakage from the absorbent article of urine or other bodily fluid leaking out of the absorbent article;
    using a camera, continuously detecting a position of the wearer;
    electronically recording wetness incidents using the signaling device, the wetness detection mat, and wearer position; and
    viewing the wetness detection indicia to detect where leakage occurred.

15. The method of claim 14, wherein the wetness detection indicia include a color-changing ink.

16. The method of claim 14, wherein the signaling device is configured to detect wetness using capacitance.

17. The method of claim 14, wherein the signaling device is adapted to be attached to the outer surface of the absorbent article.

18. The method of claim 14, wherein the signaling device includes a housing and a flexible sensor band extending from the housing.

19. The method of claim 14, wherein the camera is an imaging sensor comprising color and infrared sensors.

20. A leakage assessment system for use with an absorbent article having a body-side liner, an outer cover providing an outer surface, and an absorbent structure located between the outer cover and the body-side liner, the system comprising:
    a computer;
    a signaling device adapted to be used in conjunction with the absorbent article, the signaling device adapted to sense wetness in the absorbent article using capacitance, wherein the signaling device is in electronic communication with the computer, and wherein the signaling device is adapted to be attached to the outer surface of the absorbent article;
    a wetness detection mat in electronic communication with the computer, wherein the wetness detection mat is configured to electronically detect wetness from leakage from the absorbent article of urine or other bodily fluid leaking out of the absorbent article; and
    an image capture device configured to continuously detect an absorbent article wearer position, wherein the image capture device is in electronic communication with the computer, wherein the computer is configured to electronically record wetness incidents using the signaling device, the wetness detection mat, and the wearer position captured by the image capture device.

* * * * *